(12) United States Patent
Lawandy

(10) Patent No.: US 9,292,989 B2
(45) Date of Patent: Mar. 22, 2016

(54) TEMPERATURE ACTIVATED CHANGES TO LIGHT ABSORPTION AND EMISSION CHARACTERISTICS FOR SECURITY ARTICLES

(71) Applicant: Nabil Lawandy, Saunderstown, RI (US)

(72) Inventor: Nabil Lawandy, Saunderstown, RI (US)

(73) Assignee: SPECTRA SYSTEMS CORPORATION, Providence, RI (US)

( * ) Notice: Subject to any disclaimer, the term of this patent is extended or adjusted under 35 U.S.C. 154(b) by 23 days.

(21) Appl. No.: 14/179,844

(22) Filed: Feb. 13, 2014

(65) Prior Publication Data

US 2015/0228142 A1    Aug. 13, 2015

(51) Int. Cl.
| | |
|---|---|
| *G01N 21/64* | (2006.01) |
| *G01N 21/71* | (2006.01) |
| *G07D 7/12* | (2006.01) |
| *B82Y 40/00* | (2011.01) |

(52) U.S. Cl.
CPC ............... *G07D 7/122* (2013.01); *B82Y 40/00* (2013.01); *G01N 21/64* (2013.01); *G01N 21/71* (2013.01); *G01N 2201/061* (2013.01)

(58) Field of Classification Search
CPC ........ G01N 21/64; G01N 21/71; G07D 7/122
See application file for complete search history.

(56) References Cited

U.S. PATENT DOCUMENTS

2013/0181144 A1*   7/2013   Rapoport et al. .......... 250/459.1

* cited by examiner

*Primary Examiner* — David Porta
*Assistant Examiner* — Faye Boosalis
(74) *Attorney, Agent, or Firm* — Barlow, Josephs & Holmes, Ltd.

(57) ABSTRACT

Disclosed are security articles and methods and systems for authenticating security articles through the application if temperature related stimuli. Carefully synthesized nanostructures are formed to exhibit a large number of defect states within the bulk of the nanostructure. The large number of surface defects create a plurality of electron trap states below the conduction band of the composition and/or a plurality of hole states above the valance band such that excitations are induced by small changes in energy at or around kT. In this manner, a security article formed using the synthesized nanostructures produces measurable changes in spectral output based on small changes in temperature at or about room temperature. This allows the security article to be verified at high speeds with low power requirements for induced temperature change.

14 Claims, 4 Drawing Sheets

TEMPERATURE ACTIVATED CHANGES TO LIGHT ABSORPTION AND EMISSION CHARACTERISTICS FOR SECURITY ARTICLES

BACKGROUND OF THE INVENTION

The present invention relates generally to machine detectable security markings. More specifically, the present invention relates to security articles having light emission characteristics that change in response to small changes in temperature, whether heating or cooling.

Counterfeiting and forgery have become significant concerns in the modem economy and marketplace. Advances in computing technology and printing techniques have increased the incidence of forgeries, counterfeited documents, and other fraudulent activities. Countless areas of today's high-technology society require and rely upon certification, authentication and protection of highly valuable documents, papers, currency and other materials. Thus, there is a need for security markings to be incorporated into currency, important documents, packaging, and other authentic materials to prevent unauthorized copying, forging, counterfeiting and other fraudulent use.

A similar problem exists in a variety of contexts. In addition to protecting against counterfeit currency, authentication of valuable documents or materials also affects many facets of the economy. Authentication stamps such as visas or postmarks, for example are subject to fraudulent use and forgery. Also a wide variety of products and consumer goods may be created as knock-offs cheap replacements or gray market goods. Notaries public use a raised stamp to authenticate notarized documents. Drivers' licenses, passports and other photographic identification contain holograms and microprinting. Sporting memorabilia and retail clothiers use holographic tags and stamps to assist in proving authenticity. Even fashion designers are now including authentication devices in their clothing to prevent passing off of knock-offs as designer products.

Current methods of authentication of currency involve visual observation, scanning under ultraviolet lamps, notes containing security threads, and emissive materials such as inks and planchettes. Such security threads emit a distinct marking, color or code in response to exposure to the ultraviolet light. In some circumstances, the emissive features of different denominations of notes can emit different colors. In addition to the colors of the emission, a code number or other unique identifier can be detected by the naked eye when the note is exposed to ultraviolet light or excitation of some form.

A disadvantage to most of the traditional security features is that they are visible and known to the world. If a counterfeiter is aware there is a security thread in a bill or a watermark in a document, replication of the security feature is easier. Once a feature is made known to the public, a counterfeiter may begin to develop specific strategies and solutions to overcome the security protections provided by the specific feature. Methods of creating and perfecting forgeries and counterfeit documents have become easier and more available with the advent of highly sophisticated computer printing and processing. As far back as 1991, the United States Treasury has continually added security safeguard features to the denominations of currency in an attempt to combat the use of counterfeit money. These safeguards have included watermarks, security threads embedded in the paper, microprinting, color-shifting ink, and the use of multi-colored bills.

Accordingly, a need exists for security features that further reduce a counterfeiter's likelihood of success, even if they are aware of the existence of the security feature. There is a further need for covert optically encoded markings, formed from at least one emitter that responds differently when exposed to two varied stimuli to create a machine readable response that cannot be detected by the human eye.

BRIEF SUMMARY OF THE INVENTION

Embodiments of the invention include thermoemissive security articles and methods and systems for authenticating security articles through the application of temperature related stimuli, either heating or cooling. According to one embodiment, an illustrative security feature includes activation of a nanoscale II-VI or III-V semiconductor material having an optical signature that responds to small changes in temperature by the simultaneous presence of a source of electromagnetic radiation and variation in thermal environment. Thus, initiating a change in the spectral emission response of the activation of the material in relation to small changes in the temperature of the security feature.

In accordance with the present invention the material subject to activation is preferably a thermoemissive nanostructure synthesized to exhibit a large number of surface defect states. In particular, nanostructures having a large surface area to volume ratio exhibit a large numbers of defect states resulting from unbounded surface sites. Carefully synthesized nanostructures are formed in accordance with the present invention to exhibit a large number of defect states within the bulk of the nanostructure. The nanostructures formed have a particularly deep excitonic state for a large gap semiconductor that in turn creates a desirable material response at or near room temperature. Generally the nanostructures are preferably II-VI semiconductors, III-V semiconductors, transition metal and semiconductor doped glass and doped glass nano materials.

Ultimately the nanostructures of the present invention are formed to include large numbers of surface defects that create a plurality of electron trap states below the conduction band of the composition and/or a plurality of hole states above the valance band such that excitations are induced by small changes in energy at or around kT. In this manner, a security article formed using the synthesized nanostructures produces measurable changes in spectral output based on small changes in temperature at or about room temperature. This allows the security article to be verified at high speeds with low power requirements for induced temperature change.

Security articles, such as those described herein, may require more than one stimulus, e.g., application of both light and a change in temperature, to detect the authentication feature. Further, such security articles may have security features that can be used either publicly, covertly, or both, i.e., having a first response for public access and a second response for covert usage.

In one embodiment, the invention relates to a security article. The security article can include a host material comprising a temperature activated security feature incorporated upon or within the host material, wherein the temperature activated security feature is capable of emitting a spectral emission that changes upon exposure to a change in the temperature of the temperature activated security feature. The host material may include a polymer. The host material may include a responsive portion and a non-responsive portion, wherein the temperature activated security feature may be incorporated upon or within the responsive portion. The host material may include a reference security feature. In such a case, the security feature and the reference security feature may emit different spectral emissions upon exposure to the change in temperature. Also, in such a case, the security feature and the reference security feature may emit equivalent spectral emissions upon exposure to the change in temperature.

BRIEF DESCRIPTION OF THE DRAWINGS

These embodiments and other aspects of this invention will be readily apparent from the detailed description below and the appended drawings, which are meant to illustrate and not to limit the invention, and in which.

DETAILED DESCRIPTION OF THE INVENTION

The invention will be more completely understood through the following detailed description, which should be read in conjunction with the attached drawings. While detailed embodiments of the invention are disclosed herein, it is to be understood that the disclosed embodiments are merely exemplary of the invention, which may be embodied in various forms. Therefore, specific functional details disclosed herein are not to be interpreted as limiting, but merely as a basis for the claims and as a representative basis for teaching one skilled in the art to variously employ the invention in virtually any appropriately detailed embodiment.

In accordance with the present invention the material subject to activation is preferably a nanostructure synthesized to exhibit a large number of surface defect states. In particular, nanostructures having a large surface area to volume ratio exhibit a large numbers of defect states resulting from unbounded surface sites. Carefully synthesized nanostructures are formed in accordance with the present invention to produce measurable changes in spectral output based on small changes in temperature at or about room temperature. This allows the security article to be verified at high speeds with low power requirements for induced temperature change.

Embodiments of the invention include fluorescent or phosphorescent emissions from a security article based on small incremental changes in temperature. Specifically, synthesized nanostructures having various morphologies that exhibit a large surface area to volume ratio, when subjected to small temperature changes at or above room temperature, exhibit measurable changes in emissive output. Materials synthesized to form nanostructures under controlled conditions may be formed into nanoplates, nanorods and other large surface area to volume nanostructures. Such structures exhibit a large number of defect states resulting from unbounded surface sites. These defect states play an important role in material response at or near room temperature (0.025 eV).

By controlling the synthesis conditions of these nanostructures precisely, a large number of defect states are formed within the bulk of the nanostructure. The nanostructures formed have a particularly deep excitonic state for a large gap semiconductor that in turn creates a desirable material response at or near room temperature. Ultimately the nanostructures of the present invention are formed to include large numbers of surface defects that create a plurality of electron trap states below the conduction band of the composition and/or a plurality of hole states above the valance band such that excitations are induced by small changes in energy at or around kT.

Figure 1:
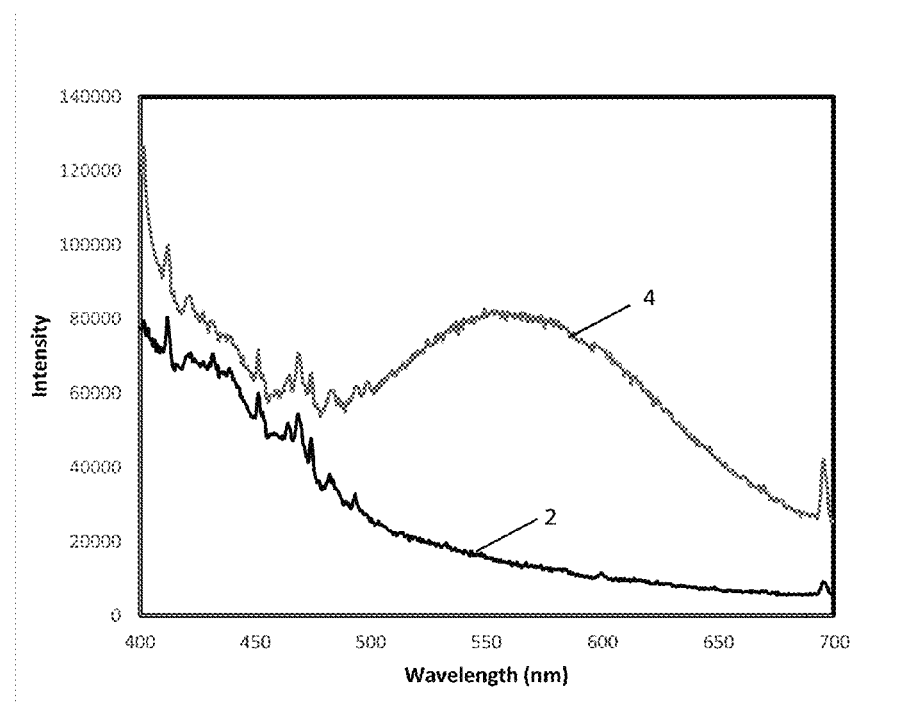
FIG. 1 is an illustrative graph of the spectral emission of a security article in accordance with an embodiment of the invention.
Figure 2:
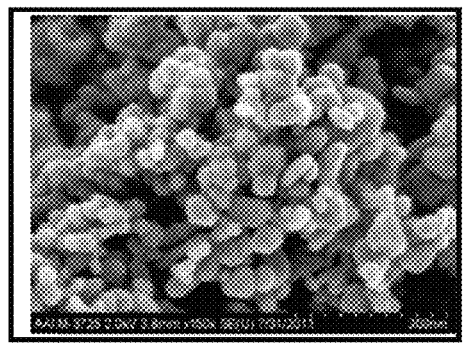
FIG. 2 is a magnified image of a common nanopowder.
Figure 3:
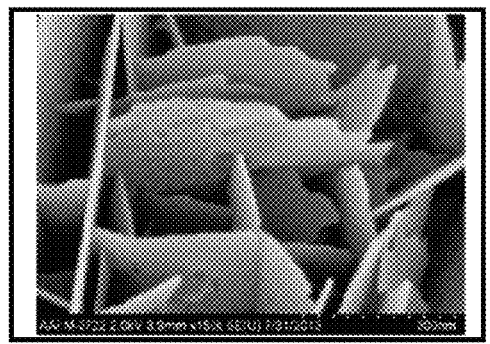
FIG. 3 is a magnified image of a synthesized nanopowder with a large surface area to volume ratio in accordance with an embodiment of the invention.

In one example, as seen at FIG. 1, as compared to the emission band 2 of commercial nanopowder materials, these defects along with the other neutral and singly ionized defects result in an emission band 4, at about 575 nm when using 365 nm excitation of the nanopowder. Commercially available nanopower can be seen at FIG. 2 in comparison to nanopowder synthesized in accordance with the present invention to form a large surface area to volume ratio that creates a large number of surface defects at FIG. 3. As can be clearly seen, the commercially available material does not exhibit the defect states emission. Analysis of these images at 300 nm/div resolution clearly shows that the material of the present invention is effectively a 2D flake or plate-like structure that is of the order of 60 nm wide on the edge, and commercial material is a nanoscale particle having grains of the order of 600 nm diameter.

Figure 4:
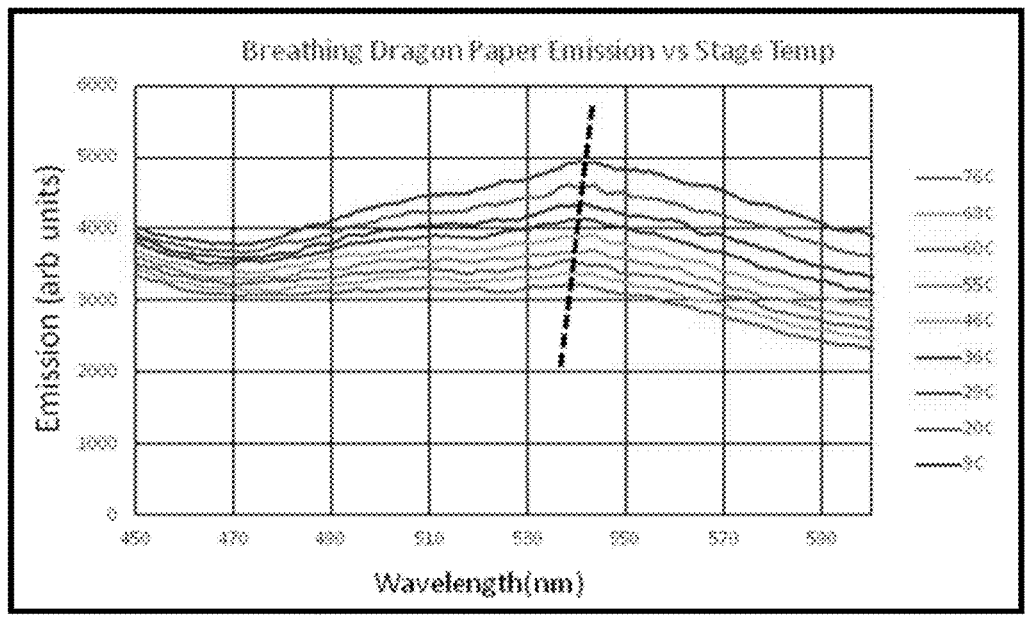
FIG. 4 is an illustrative graph of the spectral emission of a security article in accordance with an embodiment of the invention at various temperatures.
Figure 5:
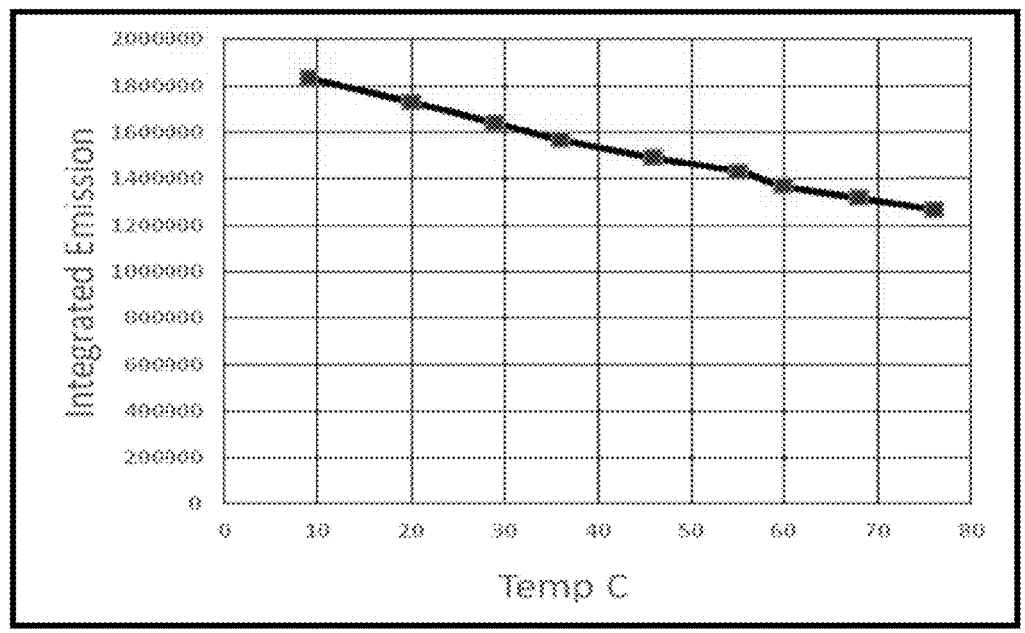
FIG. 5 depicts the change in emission of a security article relative to changes in temperature in accordance with an embodiment of the invention.

The synthesized nanopowder exhibits a strong change in emissive response related to changes in temperature with a dramatic sensitivity in the region of room temperature and in the spectral region of about 500 nm-700 nm. Paper materials, water-based and solvent-based inks impregnated with the synthesized ZnO flakes have a large variation in emission spectrum as shown at FIG. 4 as a function of changes in temperature from 9 C-76 C. Specifically, FIG. 4 shows the spectrally integrated value (arb units) as a function of temperature. Further, the data in FIG. 5 shows that the integrated light output from this material exhibits approximately a 0.5%/1 C change with temperature. This extremely high slope efficiency near room temperature implies that small changes in temperature, whether cooling or heating, will result in a measurable change in emissive output of the material.

The low temperature change requirements also shows that the effect can be implemented at high speeds. A change in emissive output of 2% only requires a temperature change of 4 C. To accomplish such a change on a 1 mm wide line, a heating rate of only $4\times10^4$ C/second. Given the heat capacities of flexographic inks and the associated thicknesses, this only requires heat fluxes of milliwatts/$m^2$ or less.

In one embodiment, exposing the security article to a change in temperature, reveals a unique spectral emission by which the security article may be authenticated. According to embodiments of the invention, excitation of the security article may include visible ambient light or sunlight, or may include other light or electromagnetic sources such as ultraviolet sources or infrared sources. Changes in temperature may be accomplished through heating elements, cooling elements or the application of a modest gas stream that induces heating or cooling.

The security article may include one or more temperature sensitive materials, which may be disposed on or within a permeable host material, such as a polymer material. The temperature sensitive material of the security article may be part of an ink, a coating, a security thread, a planchette, a particle, a hologram, or a windowed region in a document or banknote. The emission characteristics of the temperature sensitive material change with exposure to incremental heating or cooling effects. The light emission or color of the temperature sensitive material may change upon excitation with a stimulus from an electromagnetic source, e.g., ultraviolet, visible or infrared. Thus, authenticity of a security article may be determined by measuring the intensity of the security feature's spectral emission or change thereof.

Figure 6:
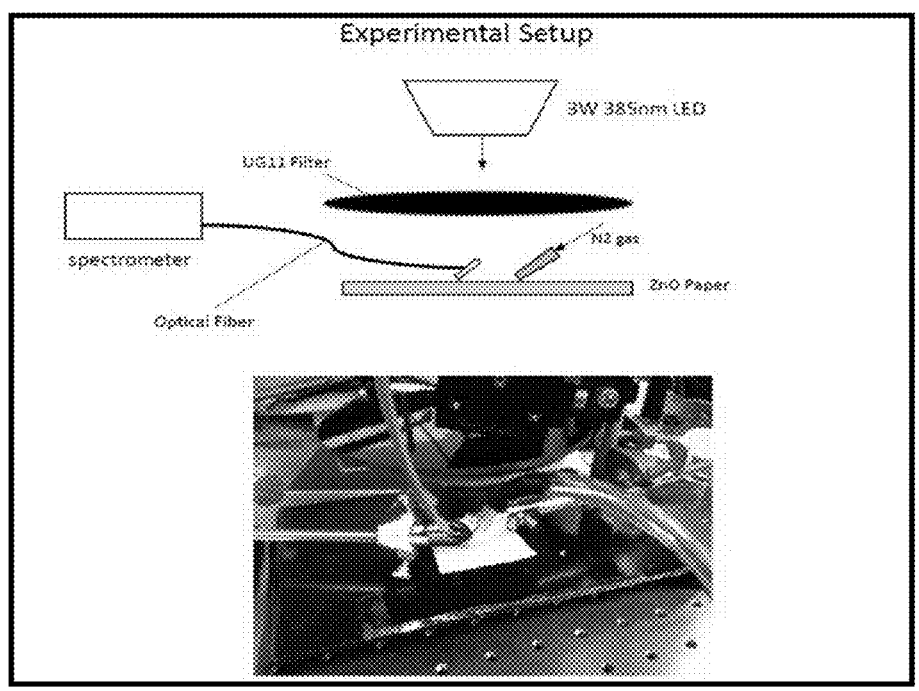
FIG. 6 schematically depicts a system for verifying the security feature of the present invention.

A schematic detector system for analyzing the security features in a security article is depicted at FIG. 6 may include an electromagnetic or light excitation source such as the 3W 385 nm LED shown, a device for spectral detection of absorption, color or emission, and a temperature altering device, such as a pump, nozzle or jet from a gas source, a heater or chiller. The detector system may also be capable of measuring the time response of the phase responses of spectral changes of the security article, e.g., with respect to periodic excitation by light or temperature change.

The spectral emissions of a security article may be used to identify and verify the authenticity of the article. A spectral emission may be illustrated by showing the intensity of the feature as a function of wavelength. A spectral emission from a typical security feature yields a signature having detectable characteristics or patterns across the wavelength spectrum. According to one embodiment of the invention, the security feature is enhanced such that excitation of the feature creates a distinct spectral pattern that may be analyzed to verify authenticity. If, upon scanning the spectral emission of the article containing the feature, the expected emissive signature does not match an expected signature, the article may be a forgery or may have been tampered with. If the signature matches the expected pattern or value, the document may be authentic.

Figure 7:
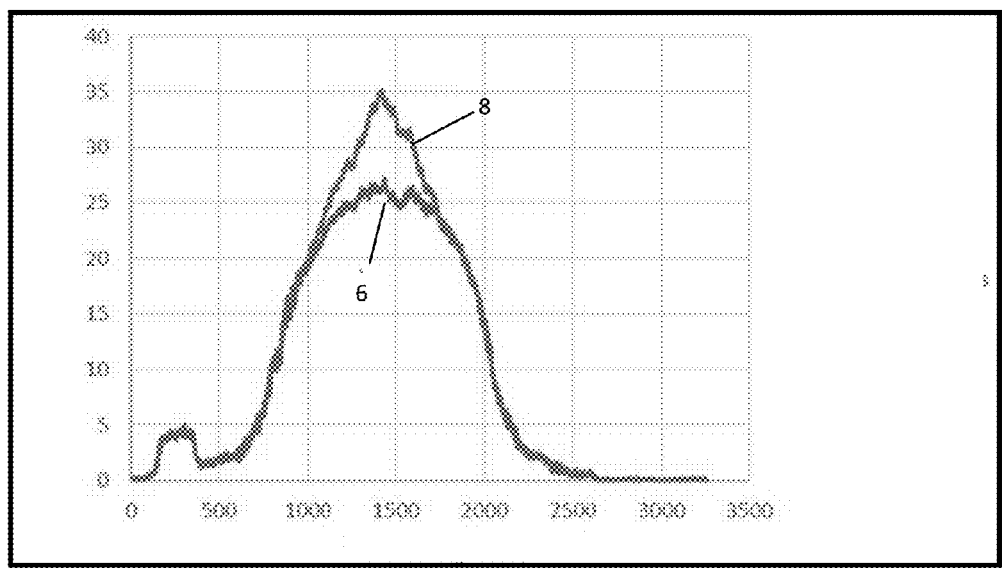
FIG. 7 is an illustrative graph depicting a change in a composite emission of a security article in accordance with an alternate embodiment of the invention.

FIG. 7 shows a spectral emission signature of a security feature in accordance with an embodiment of the invention. Specifically, FIG. 7 depicts the intensity of an emissive response from two excitation forms—one optical, one optical and thermal. A first emission 6 is the result of optical excitation of the security feature; while a second emission 8 shows a spectral signature with a measurable change in peak emission results from the excitation of the security feature with optical and thermal exposure simultaneously.

Figure 8:
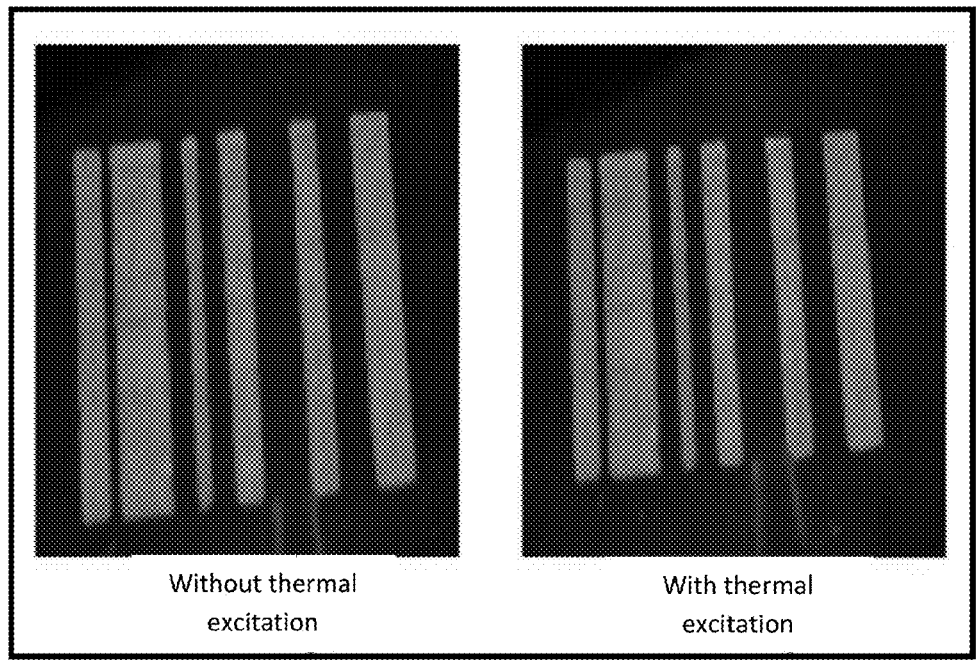
FIG. 8 depicts the application of a barcode feature to a security article in accordance with an alternate embodiment of the invention.
Figure 9:
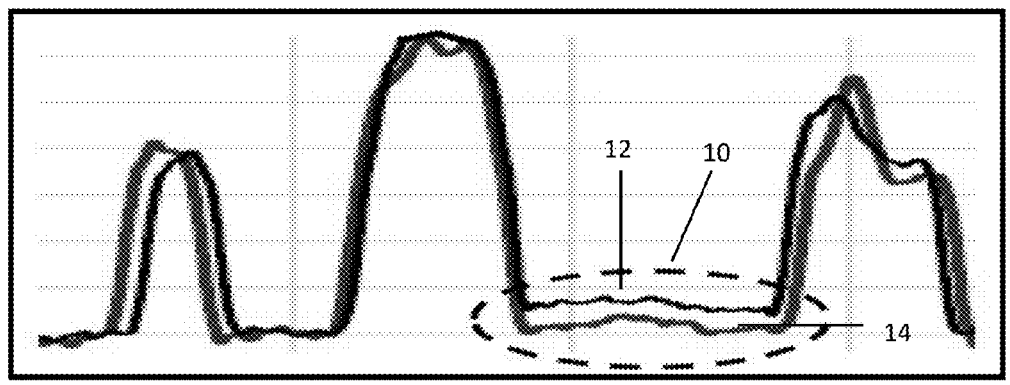
FIG. 9 depicts the response of the feature of FIG. 8.

In other embodiments a printed bar code (1D or 2D) can be embedded along with a second phosphour or upconverting system and detected by spectral filtering as authenticated via the cooling or heating effect. FIG. 8 depicts a barcode that is overlayed onto a material containing the temperature change feature of the present invention. The barcode is excited using electromagnetic stimulation to produce a fluorescent or phosphorescent spectral emission. Visually the barcode appears to produce the same emission without application of thermal stimulus (left) and with the application of thermal stimulus (right). However, with the application of thermal stimulus between the $4^{th}$ and $5^{th}$ bar of the code in FIG. 8 it can be seen at FIG. 9 in the oval region 10 that the change in the underlying temperature sensitive security feature produces a measurable change in emissive output as seen in the difference between the two spectral emission output lines 12, 14.

According to an embodiment of the invention, a machine-detectable security feature is included in a security article such as a document, currency, or secondary packaging for items such as tobacco, luxury goods, or pharmaceuticals. The security feature may be, e.g., embedded within a security thread, planchette or as part of an ink, resulting in a visible change of the excited signature of the threads when viewed using an ultraviolet source or lamp or other appropriate excitation source. Application of a controlled temperature change, however, may lead to both a color change in the security feature as well as measurable and quantifiable spectral shifts. The security feature, while undetectable to the naked eye under some circumstances, emits a specific and distinct color as well as a unique spectral fingerprint under optical and thermal excitation. Choices in different phosphors lead to different color and spectral emissions. The incorporation of a machine readable, covert feature may be implemented without any change to the public perception of the excited emission signature, thereby making forgery or duplication of the document more difficult.

While embodiments of the invention disclosed herein describe detection of emissive features under the excitation of light and thermal sources, one skilled in the art should recognize that advantages of the absorptive properties of a temperature sensitive material may be utilized as a security feature. For example, according to another embodiment of the invention, a security feature may include phosphorescent material having an absorptive spectral response at certain wavelengths under optical excitation. Application of a thermal excitation to the material results in the recovery of the emissive intensity of the material.

While embodiments of the invention disclosed herein describe detection based on specific responses to excitation sources, one skilled in art should recognize that additional parameters may be incorporated, such as the temporal decay of emissions, the spectral signature of the host, and response time and change in emission under thermal excitation, without deviating from the scope of the invention.

The aspects, embodiments, features, and examples of the invention are to be considered illustrative in all respects and are not intended to limit the invention, the scope of which is defined only by the claims. Other embodiments, modifications, and usages will be apparent to those skilled in the art without departing from the spirit and scope of the claimed invention.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be anyone of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

While the invention has been described with reference to illustrative embodiments, it will be understood by those skilled in the art that various other changes, omissions and/or additions may be made and substantial equivalents may be substituted for elements thereof without departing from the spirit and scope of the invention. In addition, many modifications may be made to adapt a particular situation or material to the teachings of the invention without departing from the scope thereof. Therefore, it is intended that the invention not be limited to the particular embodiment disclosed for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

What is claimed:

1. A security article, comprising:
   a host material comprising a temperature sensitive security feature comprising a plurality of nanostructures having a high surface area to volume ratio exhibiting a plurality of excitation defects throughout the host material, wherein the temperature sensitive security feature is capable of emitting a spectral emission that changes upon exposure to a change in temperature of the temperature sensitive security feature.

2. The security article of claim 1 wherein the host material comprises a polymer.

3. The security article of claim 1 wherein the host material is a substrate with the plurality of nanostructures disposed therein.

4. The security article of claim 1 wherein the host material is an ink with the plurality of nanostructures disposed therein, said ink further being printed onto a substrate as a security feature.

5. The security article of claim 1 wherein the host material comprises a responsive portion and a non-responsive portion, and wherein the temperature sensitive security feature is incorporated upon or within the responsive portion.

6. The security article of claim 1 wherein the temperature activated security feature is further combined with a phosphorescent or fluorescent security feature.

7. The security article of claim 6 wherein the temperature sensitive security feature and the phosphorescent or fluorescent security feature emit different spectral emissions upon exposure to the change in temperature.

8. The security article of claim 6 wherein the temperature sensitive security feature and the phosphorescent or fluorescent security feature emit equivalent spectral emissions upon exposure to the change in temperature.

9. The security article of claim 1 wherein the temperature sensitive feature has a large variation in emission spectrum as a function of changes in temperature from 9 C-76 C.

10. The security article of claim 1 wherein the temperature sensitive feature emission exhibits approximately a 0.5%/1 C change with temperature.

11. A method of authenticating a security article, comprising the steps of:
    directing electromagnetic radiation to a security article comprising a temperature sensitive security feature comprising plurality of nanostructures having a high surface area to volume ratio exhibiting large numbers of excitation defects therein;
    initiating a change in the temperature of the security feature; and
    detecting a differential spectral emission of the security feature resulting from the change in temperature.

12. The method of claim 11 wherein the step of initiating a change in the temperature of the security feature comprises introducing a flow of gas to the security feature.

13. The method of claim 11 further comprising the step of comparing the differential spectral emission with an expected spectral emission to determine authenticity of the security article.

14. The method of claim 11 further comprising the step of:
    detecting a spectral emission from a phosphorescent or fluorescent security emission in overlying relation with said temperature sensitive security feature;
    initiating a change in the temperature of the temperature sensitive security feature; and
    detecting a differential spectral emission of the combined security features resulting from the change in temperature.

* * * * *